US00PP20119P2

(12) United States Plant Patent
Klemm

(10) Patent No.: US PP20,119 P2
(45) Date of Patent: Jun. 23, 2009

(54) ***PETUNIA* PLANT NAMED 'KLEPH07145'**

(50) Latin Name: *Petunia*
Varietal Denomination: KLEPH07145

(75) Inventor: Nils Klemm, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/082,037

(22) Filed: Apr. 7, 2008

(51) Int. Cl.
*A01H 5/00* (2006.01)

(52) U.S. Cl. ..... Plt./356

(58) Field of Classification Search ..... Plt./356
See application file for complete search history.

*Primary Examiner*—Susan B McCormick Ewoldt
(74) *Attorney, Agent, or Firm*—Jondle & Associates, P.C.

(57) ABSTRACT

A new cultivar of *Petunia* particularly characterized by its double, light lemon-colored flowers and its compact, semi-upright growth habit, is disclosed.

1 Drawing Sheet

Genus and species: *Petunia* hybrid.
Variety denomination: 'KLEPH07145'.

BACKGROUND OF THE NEW PLANT

The present invention comprises a new and distinct cultivar of *Petunia,* botanically known as *Petunia* hybrid, and hereinafter referred to by the cultivar name 'KLEPH07145'. 'KLEPH07145' was discovered as a seedling resulting from a cross conducted in summer 2004 in Stuttgart, Germany between the female *Petunia* parent, 'KLEPH05117' (U.S. Plant Pat. No. 18,590) and the proprietary male *Petunia* parent, 'W 115' (unpatented). A single plant selection was subsequently chosen for further evaluation and for asexual propagation.

The new cultivar was created in 2004 in Stuttgart, Germany and has been asexually reproduced repeatedly by vegetative cuttings and in-vitro propagation in Stuttgart, Germany over a three-year period (more than 45 generations). 'KLEPH07145' has been found to retain its distinctive characteristics through successive asexual propagations.

SUMMARY OF THE INVENTION

The following are the most outstanding and distinguishing characteristics of this new cultivar when grown under normal commercial practices in a greenhouse in Stuttgart, Germany.

1. Double, light lemon-colored flowers; and
2. Compact and semi-upright growth habit.

DESCRIPTION OF THE PHOTOGRAPH

This new *Petunia* plant is illustrated by the accompanying photograph which shows foliage and a close-up of the mature flower; the colors shown are as true as can be reasonably obtained by conventional photographic procedures. The photograph is of a plant about 5-months old and grown from rooted cuttings in an 11-cm pot under greenhouse (glasshouse) in Stuttgart, Germany under conditions which approximate those generally used in commercial practice.

DESCRIPTION OF THE NEW CULTIVAR

The following detailed descriptions set forth the distinctive characteristics of 'KLEPH07145'. The data which define these characteristics were collected from asexual reproductions carried out in Stuttgart, Germany. The plant history was taken on 5-month-old plants in 11-cm pots that were pinched once approximately one week after potting and grown in a greenhouse in the spring. The color readings were determined under natural light. Color references are to the RHS Colour Chart of The Royal Horticultural Society of London (RHS) (2001).

DESCRIPTION OF THE NEW PLANT

Classification:
- *Family.*—Solanaceaece.
- *Genus and species.*—*Petunia* hybrid.
- *Common name.*—*Petunia.*

Parentage:
- *Female parent.*—The yellow-flowered *Petunia* 'KLEPH05117' (U.S. Plant Pat. No. 18,590).
- *Male parent.*—The proprietary lemon-flowered *Petunia* 'W 115' (unpatented).

Plant:
- *Form.*—Compact.
- *Habit.*—Semi-upright.
- *Height* (*from top of soil*).—4.0 cm.
- *Width* (*horizontal plant diameter*).—18.0 cm.
- *Propagation.*—Vegetative propagation by terminal tip cuttings or in vitro propagation of shoot tips.
- *Time to produce a finished flowering plant.*—14 weeks.
- *Time to initiate and develop roots.*—19 days.
- *Root description.*—Moderate density and freely branching, white roots.

Stems:
- *Average number* (*basal*).—6.
- *Length of basal branches* (*from the base of the stem to the tip*).—9.0 cm.
- *Internode length.*—0.5 cm to 3.5 cm.
- *Diameter of branches* (*from midpoint*).—1.0 cm to 6.0 cm.
- *Stem color.*—RHS 137B.
- *Anthocyanin.*—Absent.

*Texture.*—Smooth.

Leaves:

*Arrangement.*—Alternate.

*Size.*—Length: 0.5 cm to 4.0 cm. Width: 0.5 cm to 3.5 cm.

*Shape.*—Broadly elliptic.

*Margin.*—Weak undulation.

*Apex.*—Broadly acute.

*Base.*—Obtuse.

*Immature leaf.*—Color: Upper surface: RHS 139B. Lower surface: RHS 139C.

*Mature leaf.*—Color: Upper surface: RHS 147B. Upper surface: RHS 147B.

*Texture.*—Smooth.

*Venation.*—Pinnate.

*Venation color.*—Upper surface: RHS 145A. Lower surface: RHS 145B.

*Petioles.*—Length: 0.3 cm to 2.8 cm. Diameter: 0.3 cm. Color (both upper and lower parts): RHS 138B. Texture: Smooth.

Flower bud:

*Shape.*—Irregular to oblong.

*Size.*—Length: 5.0 cm. Diameter: 2.3 cm.

*Color at tight bud.*—RHS 154C.

*Immature flower color.*—RHS 154D.

*Texture.*—Pubescent.

Inflorescence:

*Blooming habit* (*flowering season*).—Continuous flowering during the summer.

*Inflorescence type.*—Double flowers.

*Number of flowers per node.*—1.

*Lastingness of individual blooms on the plant.*—6 days.

*Fragrance.*—Absent.

*Pedicels.*—Color: RHS 137C. Length: 1.6 cm. Diameter 0.2 cm.

*Texture.*—Smooth.

Flowers:

*Shape.*—Carnation-shaped.

*Size.*—Diameter (flower face): 6.0 cm. Depth (total length of flower): 4.0 cm. Funnel: Length: 3.5 cm. Diameter (at opening): 0.3 cm. Outside texture: Smooth.

*Mature flower.*—Face/Margin Color: Upper surface: RHS 1C. Lower surface: RHS 1D. Corolla tube: Color inside (throat): RHS 1C. Color outside: RHS 1D. Petals: Apex: Rounded to emarginate. Base: Reniform. Margin: Undulating. Waviness: Strong. Lobation: Strong. Texture: Smooth.

*Calyx arrangement.*—One star-shaped calyx tube with five sepals fused at the base per flower.

*Sepals.*—Number: 5. Color RHS 138A. Length: 2.1 cm. Width: 0.4 cm. Shape: Lanceolate to elliptic. Apex: Obtuse. Base: Fused. Margin: Entire. Texture: Smooth.

Reproductive organs:

*Stamens.*—Quantity: Varies from 0 to 5. Shape: Needlelike with elliptic head. Filament: Length: 0.3 cm. Diameter: 0.1 cm. Color: RHS 1D. Anther: Shape: Elliptic. Color: RHS 1D. Length: 0.2 cm. Diameter: 0.2 cm. Pollen: Color: RHS 1D. Amount: Sparse.

*Pistils.*—Number: 1. Length: 0.3 cm. Diameter: 0.1 cm. Stigma: Color: RHS 150A. Shape: Oval. Length: 1.1 cm. Diameter: 0.1 cm. Style: Color: RHS 150C. Length: 1.2 cm. Diameter: 0.1 cm. Texture: Fibrous.

Fruit and seed set: None observed.

Disease and insect resistance: Not observed.

COMPARISON WITH PARENTAL AND COMMERCIAL CULTIVARS

'KLEPH07145' differs from the female parent, the *Petunia* 'KLEPH05117' (U.S. Plant Pat. No. 18,590), in that 'KLEPH07145' has a double flower, while 'KLEPH05117' has a single flower. In addition, 'KLEPH07145' has a light lemon-colored flower, while 'KLEPH05117' has a yellow-colored flower.

'KLEPH07145' differs from the male parent, the proprietary *Petunia* 'W 115' (unpatented), in that, 'KLEPH07145' has a double flower, while 'W 115' has a semi-double flower. In addition, 'KLEPH07145' has a lighter flower color than 'W 115'.

'KLEPH07145' differs from the commercial comparison variety 'KLEC04065' (U.S. Plant Pat. No. 18,364) in that 'KLEPH07145' has a compact, semi-upright growth habit, while 'KLEC04065' has a less compact, more upright growth habit.

I claim:

1. A new and distinct cultivar of *Petunia* plant as shown and described herein.

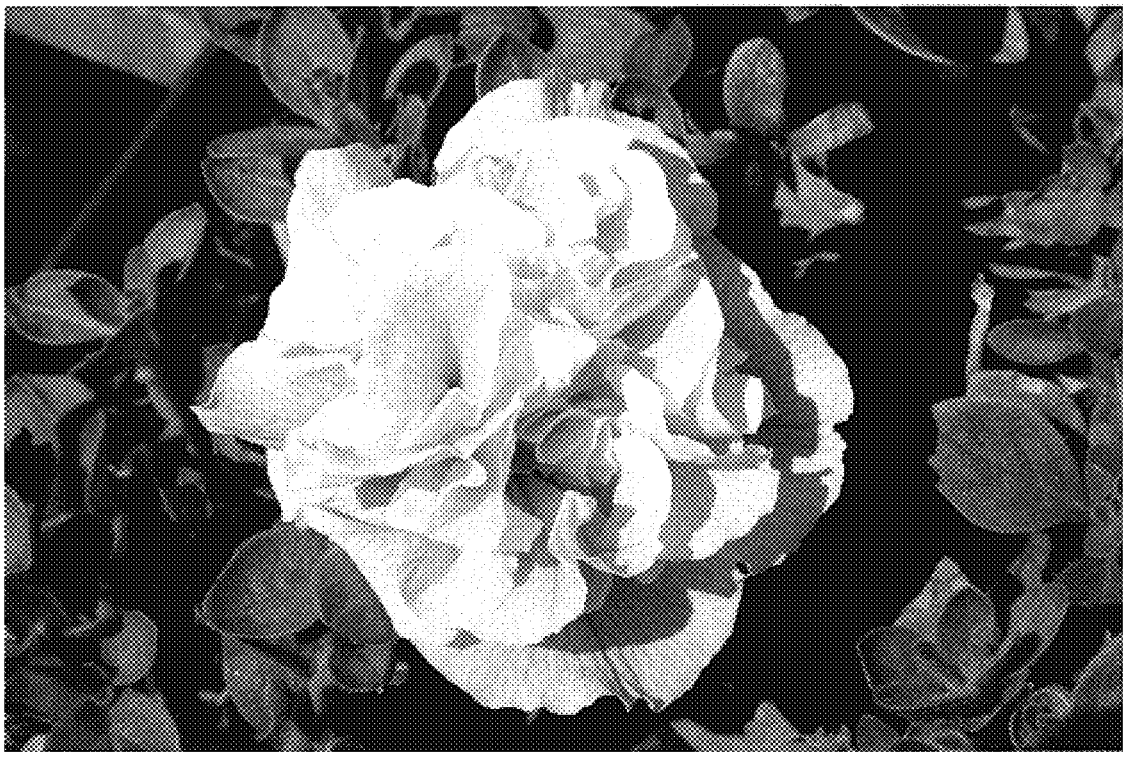

* * * * *